(12) United States Patent
Gerder et al.

(10) Patent No.: US 7,301,452 B2
(45) Date of Patent: Nov. 27, 2007

(54) CARE DEVICE WITH WIRELESS DATA COMMUNICATION

(75) Inventors: Henning Gerder, Lübeck (DE); Ali Pourrad, Klein Wesenberg (DE)

(73) Assignee: Dräger Medical AG & Co. KGaA (DE)

( * ) Notice: Subject to any disclaimer, the term of this patent is extended or adjusted under 35 U.S.C. 154(b) by 253 days.

(21) Appl. No.: 11/218,248

(22) Filed: Sep. 1, 2005

(65) Prior Publication Data
US 2006/0049937 A1 Mar. 9, 2006

(30) Foreign Application Priority Data
Sep. 9, 2004 (DE) ............... 10 2004 043 653

(51) Int. Cl.
*G08B 1/08* (2006.01)
(52) U.S. Cl. .................. 340/539.12; 340/573.1
(58) Field of Classification Search ........... 340/539.12, 340/573.1; 600/300
See application file for complete search history.

(56) References Cited

U.S. PATENT DOCUMENTS 6,443,885 B1 9/2002 Schuler

2005/0215845 A1* 9/2005 Mahony et al. ............... 600/22

FOREIGN PATENT DOCUMENTS

DE 199 60 989 C2 7/2001

* cited by examiner

*Primary Examiner*—Jeffery Hofsass
*Assistant Examiner*—Shirley Lu
(74) *Attorney, Agent, or Firm*—McGlew and Tuttle, P.C.

(57) ABSTRACT

A care device and process are provided. The care device has a sensor module (11), which is to be placed directly on the patient (3) for picking up the patient's data, such as temperature, pulse and ECG. A first receiving means (13) is arranged in space in the vicinity of the patient (3) and is designed to pass on the measured data received from the sensor module (11). A mobile part (9) can be removed from the care device and provides wireless communication and a second receiving means (24) for establishing an alternative primary wireless link when the patient is removed from the care device.

20 Claims, 4 Drawing Sheets

CARE DEVICE WITH WIRELESS DATA COMMUNICATION

CROSS REFERENCE TO RELATED APPLICATION

This application claims the benefit of priority under 35 U.S.C. § 119 of German Application DE 10 2004 043 653.3 of Sep. 9, 2004, the entire contents of which application is hereby incorporated by reference in its entirety.

FIELD OF THE INVENTION

The present invention pertains to a care device with wireless data communication and to a process for transmitting measured data of a patient to the care device.

BACKGROUND OF THE INVENTION

A care device for closed care, in which a patient is lying within a hood and is supplied with a predetermined air temperature and humidity, is known from DE 199 60 989 C2 (see also related U.S. Pat. No. 6,443,885 which is incorporated herein by reference in its entirety). It is possible in the case of the prior-art device to remove the patient from the hood so that he or she can lie in direct skin contact with the mother or the father. This kind of care is called "kangaroo care." With the hood opened, the care device is automatically controlled in this mode of operation such that false alarms are avoided.

The prior-art care device is normally operated in the mode of operation of skin temperature control. The set point of a preset skin temperature of the patient is compared here with the measured values of at least one temperature sensor on the patient's skin. The heating within the hood is set such that deviations between the measured and predetermined temperatures are minimized. The drawback is that the temperature sensors, which are bound to the skin, are connected with the control device of the care device via sensor wires, which greatly limits the range of action upon removal of the patient. On the other hand, the sensor wires can be extended to a limited extent only because of the weak measured signals, which also fails to solve the problem of the lack of mobility.

Even though it would also be possible to transmit the measured temperature values in a wireless manner, the maximum transmitting power for the most unfavorable constellation would always have to be selected in case of variable distance, because the case in which the care staff moves away from the care device together with the patient in order to briefly perform therapeutic procedures or examination at another location is also to be taken into account.

SUMMARY OF THE INVENTION

The basic object of the present invention is to provide a care device which makes possible the greatest possible flexibility in the treatment of the patient with the lowest possible load and to provide a process for transmitting measured data of a patient to the care device.

According to the invention, a care device is provided with a control device for generating a temperature-controlled zone in the environment of a patient. A sensor module is provided to be placed directly on the patient which comprises at least one sensor for picking up the patient's data, such as temperature, pulse and ECG (Electrocardiogram). The device also has a power supply unit and a transmitter with a low power for establishing a primary radio (i.e., wireless) link. A first receiving means is arranged in space in the vicinity of the patient and is designed to pass on the measured data received from the transmitter of the sensor module to the control device. A mobile part is provided that can be removed from the care device and which has means for wireless communication with the control device. This may be in the form of a secondary radio (i.e., wireless) link with a second receiving means for establishing an alternative primary radio link with the sensor module.

According to another aspect of the invention, a process is provided for the wireless transmission of measured data of a sensor module arranged at a patient to an associated care device. The process includes the steps of arranging a first receiving means, which is designed to receive the measured values transmitted from the sensor module, in space in the vicinity of the patient. The measured values are transmitted to the care device. A removable mobile part is provided, which has means for wireless communication with the care device and has a second receiving means for receiving the measured data sent by the sensor module. The measured data of the patient is transmitted via the mobile part to the care device when the patient is removed from the care device.

The advantage of the present invention is essentially that sensor modules with low transmitting power, which operate in a wireless manner, are used, which directly communicate with a receiving means at the care device unidirectionally when the patient is located on the bed of the device. If the patient is removed from the care device, a radio link to the care device is established for the sensor modules via a mobile part being carried by the user, so that the measured data can also be transmitted when the contact with the receiving means in the care device is interrupted. The limitation of the sensor modules to a low transmitting power has the advantage that the patient is exposed to electromagnetic radiation only to a very limited extent. In addition, the power supply unit of the sensor modules is used only slightly due to the low transmitting power and the unidirectional data transmission, so that the measured data can be acquired over a very long period of time without changing the batteries. By contrast, a higher transmitting power may be present at the mobile part, which passes on measured data to the care device in the form of an intermediate station when the patient is removed from the care device. This is because the mobile part is carried on the body of the caregiver at a sufficiently great distance from the patient. Only the comparatively short distance from the receiving means of the mobile part must be bridged over by the sensor module of the patient. The greatest possible mobility is thus guaranteed. The mobile part is preferably designed for bidirectional data exchange. However, unidirectional operation is also possible. To reduce the capacity of the battery, it is possible to adapt the transmitting power to the distance from the care device, which is to be bridged over. Increased transmitting power is activated only in case of greater distances.

The change from the primary radio link at the care device to an alternative primary radio link via the mobile part is advantageously carried out by means of a switchover means.

This switchover means may be a push button actuated by the user, which is arranged on the operating unit of the care device. This push button is provided, for example, with the labeling "kangaroo care."

As an alternative, the switchover means is a switching contact on the charging cradle of the mobile part, which is actuated when the mobile part is removed or returned, or the opening or closing of the incubator hood is detected in an incubator in case of closed care.

The transmitter of the sensor module is designed such that it is suitable for bridging over a distance of at least 50 cm. A transmitting power of 25 µW is sufficient for this.

The wireless radio link is advantageously established by means of infrared light or high frequency.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
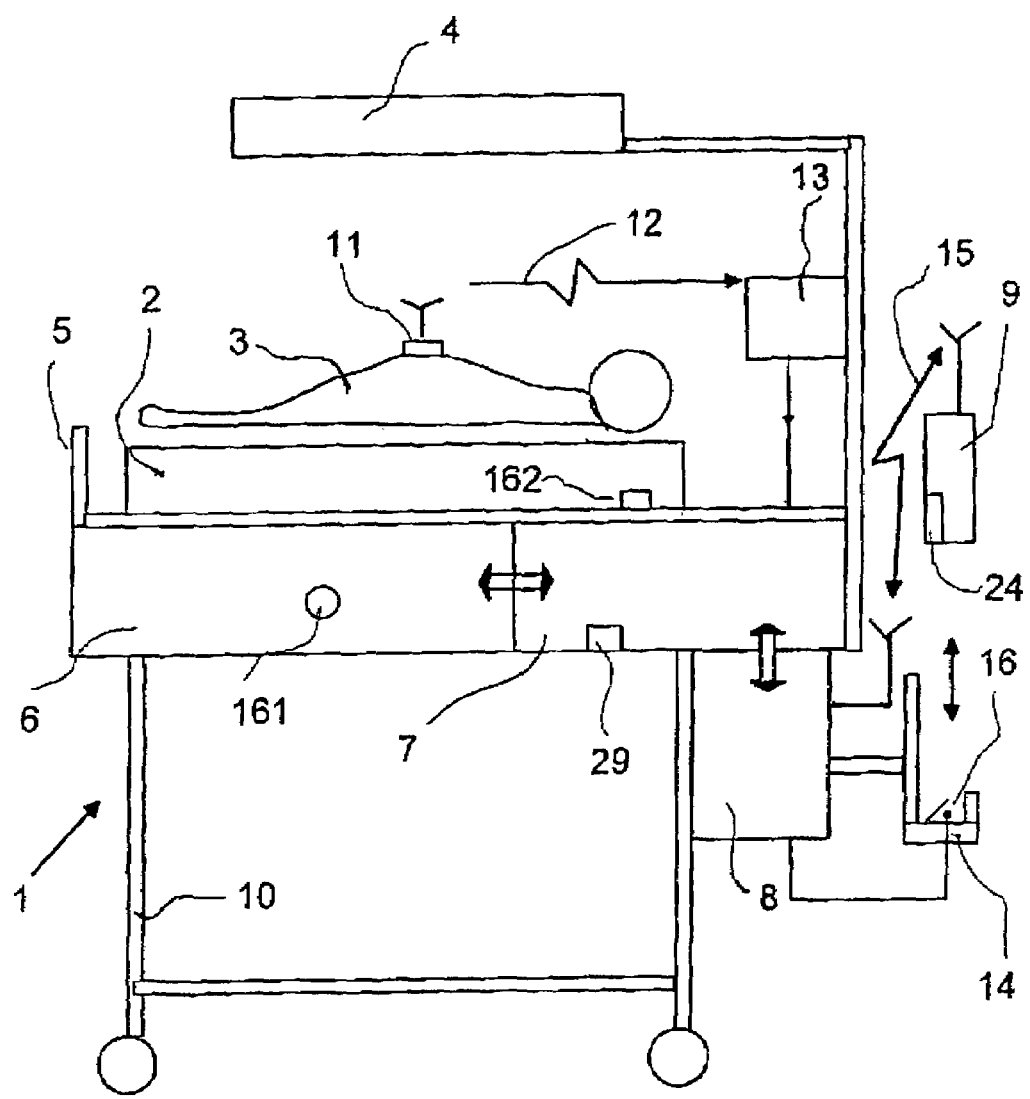
FIG. 1 is a schematic view showing the design of a care device for open care according to the invention.

Referring to the drawings in particular, FIG. 1 schematically shows a first care device 1 for open care, in which a radiant heater 4 is arranged above the patient 3 lying on a bed 2. The bed 2 is surrounded by side walls 5. The side walls 5 can be folded down from the first care device 1 before the patient 3 is removed.

The first care device 1 contains an operating unit 6, from which all settings and monitoring measures are carried out, a control device 7, which generates a temperature-controlled zone in the environment of the patient 3 together with the radiant heater 4, and a transmitting-and-receiving means 8 for bidirectional wireless communication with a mobile part 9, which can be removed from the first care device 1. The bed 2 can be adjusted to the desired working height by means of a height-adjustable chassis 10. The body temperature of the patient 3 is detected by a sensor module 11 and transmitted via a unidirectional, primary radio (wireless) link 12 to a first receiving means 13, which passes on the measured data to the control device. The mobile part 9, which can be removed from a charging cradle 14, communicates bidirectionally with the transmitting-and-receiving means 8 via a secondary radio (wireless) link 15. The removal of the mobile part 9 from the charging cradle 14 is recognized by means of a switching contact 16. As an alternative or in addition to the switching contact 16, the intended removal of the patient 3 can be entered via a push button 161 actuated by the user on the operating unit 6 or a switch 162 at the bed 2, which said switch responds to the own weight of the patient 3, or a switch 163 responding to the opening of a hood 27, FIG. 4.

Figure 2:
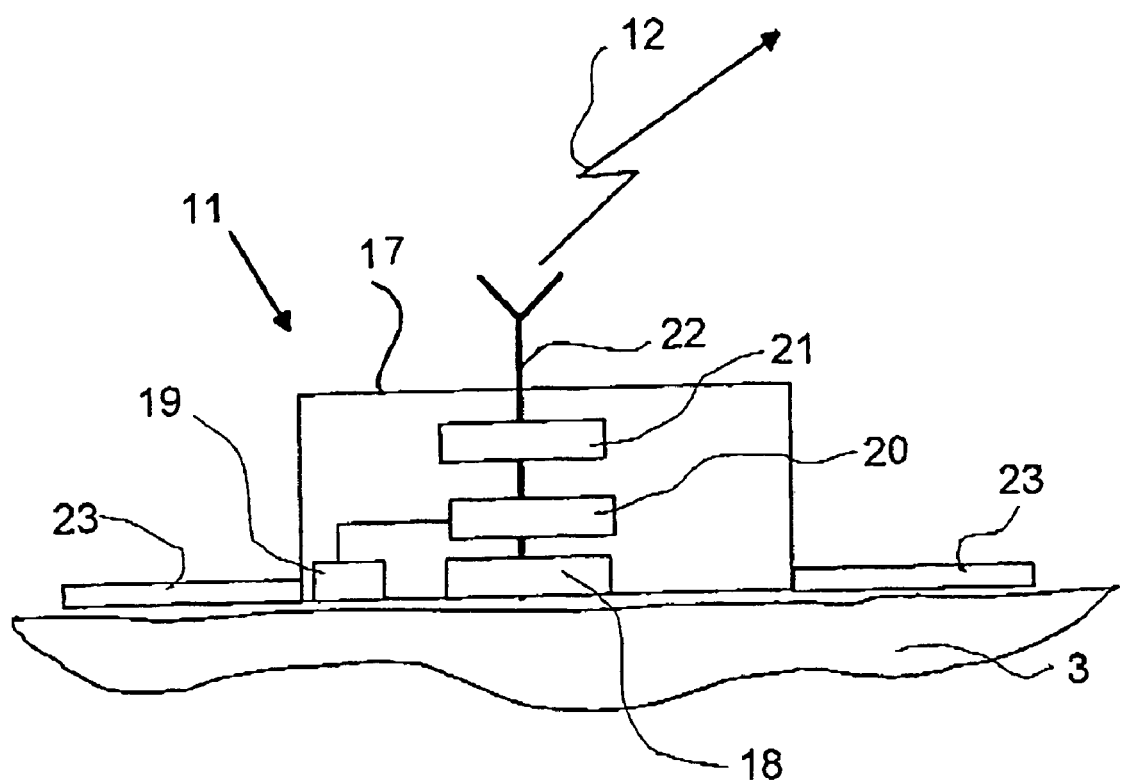
FIG. 2 is a schematic view showing the design of a sensor module according to the invention.

FIG. 2 schematically illustrates the design of the sensor module 11. A temperature sensor 18, a power supply unit 19, a signal processing unit 20, and a transmitter 21 with a transmitting antenna 22 are accommodated in a housing 17 of the sensor module 11. The housing 17 is fastened to the skin of the patient 3 by means of adhesive tape 23. The measured temperature data are formatted in the signal processing unit 20 and are transmitted together with an identification number of the sensor module 11 via the primary radio link 12. The transmitter 21 has a transmitting power on the order of magnitude of 25 µW.

Figure 3:
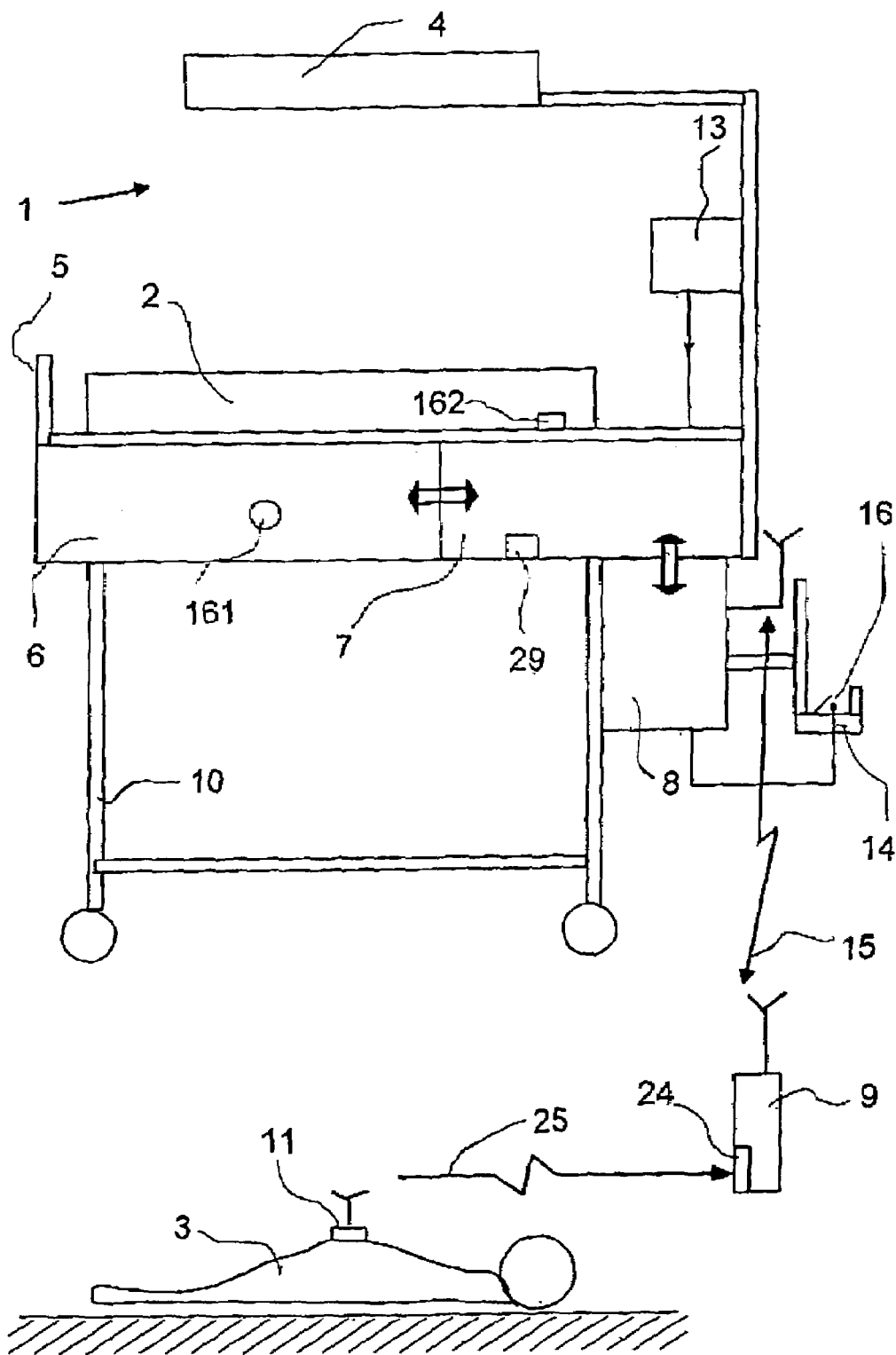
FIG. 3 is a schematic view showing the care device according to FIG. 1, in which the patient is located outside the care device.

FIG. 3 shows the first care device 1 with the patient 3, who is located outside the first care device 1. The data exchange between the sensor module 11 and the transmitting-and-receiving means 8 of the first care device 1 is established now via the mobile part 9 by establishing an alternative primary radio link 25 between the sensor module 11 and a second receiving means 24 at the mobile part 9. The secondary radio link 15 between the mobile part 9 and the transmitting-and-receiving means 8 of the first care device 1 is designed in terms of the power data such that the user can move away from the first care device 1 together with the mobile part 9 and the patient 3 without the connection being interrupted. The mobile part 9 is fastened for this application to the clothing of the user, so that only a short distance must be bridged over between the sensor module 11 and the second receiving means 24 at the mobile part 9.

Figure 4:
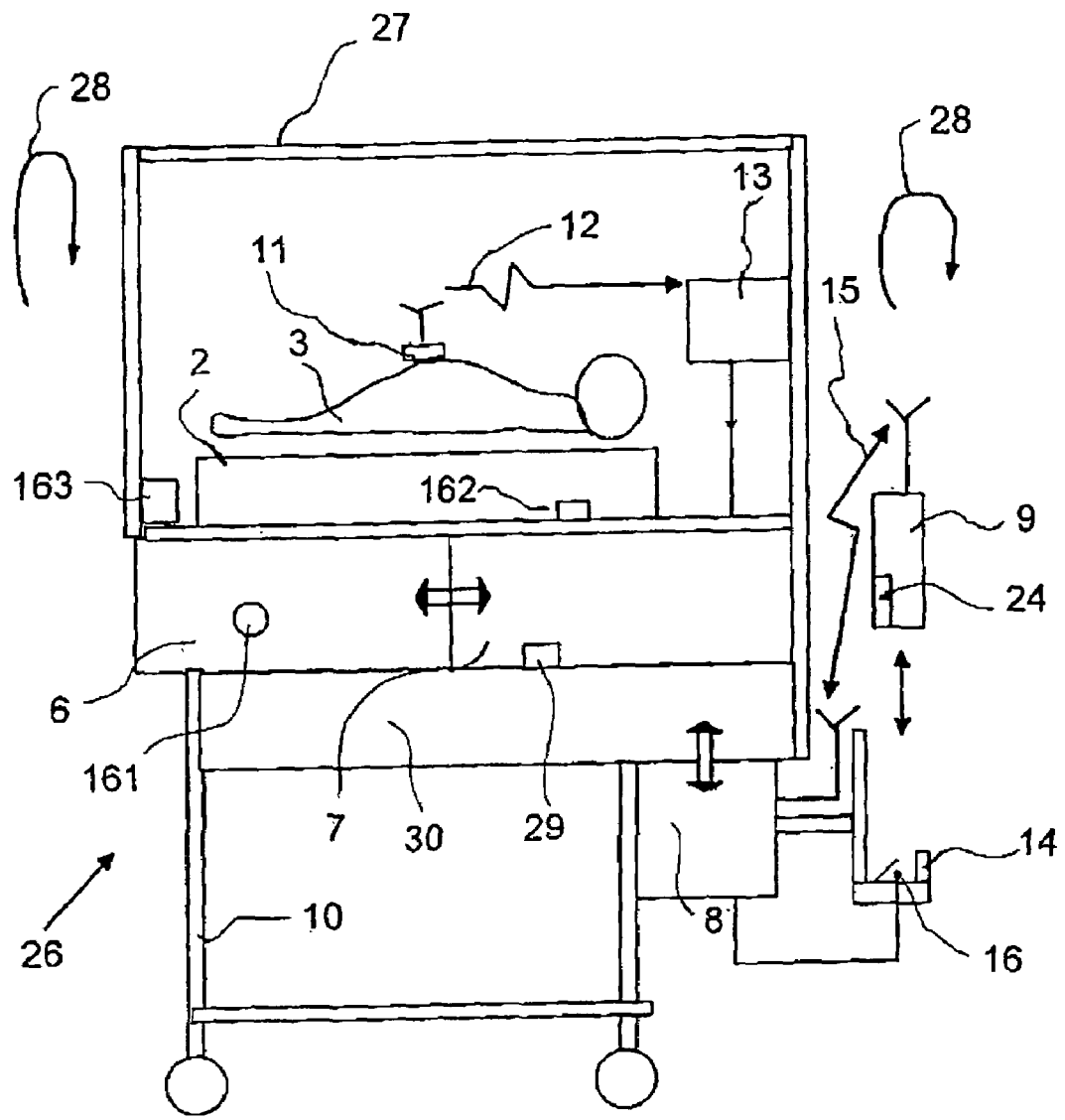
FIG. 4 is a schematic view showing the design of a care device for closed care according to the invention.

FIG. 4 schematically shows the design of a second care device 26 in the form of an incubator for closed care. Identical components are designated by the same reference numbers as in FIGS. 1 and 3. To generate the temperature-controlled zone in the environment of the patient 3, an air conditioning means 30 is provided, which contains a recirculating fan, not specifically shown, with which a predetermined temperature and moisture ratio can be set in the hood 27 surrounding the patient 3. To introduce or remove the patient 3, parts of the hood 27 or even the entire hood 27 is folded up along the arrows 28. The folding up of the hood 27 is detected by means of the switch 163.

The care devices 1, 26 for open and closed care operate as follows:

After being switched on, the care devices 1, 26 activate the primary radio link 12 and the secondary radio link 15 in a self-test and send a status display via the operating unit 6. The sensor module 11 is then fastened to the body of the patient 3 and the patient 3 is placed into the care device 1, 26, and the transmitter 21 of the sensor module 11 enters the range of reception of the first receiving means 13. The measured data and the identification number of the sensor module 11 are displayed on the operating unit 6 of the care device 1, 26. The user then confirms the combination of measured data and the identification number of the sensor module 11. The identification number of the sensor module 11 is stored in a memory 29 of the care device 1, 26. The sensor module 11 is now connected via the primary radio link 12 with the control device 7 of the care device 1, 26. The measured temperatures and the status of the primary radio link 12 are displayed on the operating unit 6 of the care device 1, 26.

The removal of the patient 3 from the care device 1, 26 is carried out as follows:

The side walls 5 are folded down in the case of the first care device 1 for open care, and the radiant heater 4 is either adjusted to a lower temperature or is switched off completely. The user then actuates the push button 161 on the operating unit 6, which designates the "kangaroo care," in order to make preparations for the removal of the patient 3 from the first care device 1. The wish to remove the patient is recognized and the secondary radio link 15 between the mobile part 9 and the transmitting-and-receiving means 8 of the first care device 1 is initialized.

In the case of the second care device 26 for closed care, the hood 27 is first opened along the arrow 28, the opening movement of the hood 27 being recognized by means of the switch 163. The secondary radio link 15 between the mobile part 9 and the transmitting-and-receiving means 8 of the second care device 26 is then initialized.

The mobile part 9 is now removed from the charging cradle 14, the removal being recognized by means of the switching contact 16. The mobile part 9 now activates the second receiving means 24 for establishing the alternative primary radio link 25. The plausibility of the measured data received from the sensor module 11 is checked in the mobile part 9 by means of the identification number. If the identification number received agrees with the identification number stored in the memory 29, the measured data of the sensor module 11 are transmitted to the control device 7 of the care device 1, 26 over two pathways, namely, the first receiving means 13 and the second receiving means 24. The patient 3 is now removed. The user can now move away from the care device 1, 26 together with the patient and as soon as the range of reception of the first receiving means 13 is left, this is displayed on the mobile part 9. After the removal of the patient 3, it is useful to close the hood 27 again in the case of the second care device 26 and subsequently to adjust the temperature to a predetermined interior temperature. The measured data now reach the care device 1, 26 via the alternative primary radio link 25 and the secondary radio link 15. However, as soon as the user leaves the range of the secondary radio link 15 with the patient 3, a multistep warning report is sent via the mobile part 9.

When the patient 3 is returned into the care device 1, 26, the sensor module 11 enters the range of reception of the first receiving means 13, and the primary radio link 12 is again established. The data of the sensor module 11 now temporarily enter the control device 7 of the care device 1, 26 via both the first receiving means 13 and the second receiving means 24. The mobile part 9 is then plugged into the charging cradle 14, which is recognized by means of the switching contact 16. Both the measured data and the identification number of the sensor module 11 reach the first receiving means 13 via the primary radio link 12. The identification number received is again compared first with the identification number being stored in the memory 29. The agreement of the data is confirmed by the user on the operating unit 6.

The care device 1, 26 is now brought into the ready-to-operate state, in which the side flaps 5 are folded up and the radiant heater 4 is activated in the case of open care in the first care device 1. The hood 27 is lowered and the temperature control is set to the measured body temperature in case of the second care device 26 for closed care. The deactivation of the special "kangaroo mode" is proposed to the user via the operating unit 6. The user confirms the changeover of the mode of operation by pressing the push button 161. The mobile part 9 will thereafter deactivate its transmission operation, and the secondary radio link 15 is switched off. The sensor module 11 is now connected with the care device 1, 26 via the primary radio link 12.

While a specific embodiment of the invention has been shown and described in detail to illustrate the application of the principles of the invention, it will be understood that the invention may be embodied otherwise without departing from such principles.

What is claimed is:

1. A care device comprising:
    a control device for generating a temperature-controlled zone in the environment of a patient;
    a sensor module to be placed directly on the patient, said sensor module including at least one sensor for picking up the patient's data including at least one of temperature, pulse and ECG, a power supply unit and a transmitter with a low power for establishing a primary radio link;
    a first receiving means arranged in space in the vicinity of a patient region, said first receiving means for passing on measured patient's data received from said transmitter of said sensor module to said control device;
    a mobile part adapted to be removed or moved away from the care device, said mobile part having means for wireless communication with said control device in the form of a secondary radio link and a second receiving means for establishing an alternative primary radio link with said sensor module.

2. A care device in accordance with claim 1, further comprising a switchover means for changing over from said primary radio link to said alternative primary radio link.

3. A care device in accordance with claim 2, wherein said switchover means is a push button actuated by a user.

4. A care device in accordance with claim 2, further comprising a charging cradle for charging said mobile part wherein said switchover means is a switching contact at said charging cradle, said switching contact responding when said mobile part is removed from said charging cradle or is returned to said charging cradle.

5. A care device in accordance with claim 2, wherein said switchover means is a switch responding to an opening or closing of a hood or the weight of the patient.

6. A care device in accordance with claim 1, wherein said transmitter of said sensor module is designed to bridge over a distance of at least 50 cm.

7. A care device in accordance with claim 1, wherein said radio links are established by means of infrared light or high frequency.

8. A process for the wireless transmission of measured data of a sensor module arranged at a patient to a care device, the process comprising the steps of:
    providing a first receiving means to receive the measured data values transmitted from the sensor module;
    arranging the first receiving means in the vicinity of the patient;
    transmitting measured values to said care device;
    providing a removable mobile part having means for wireless communication with the care device and having a second receiving means for receiving measured data sent by the sensor module; and
    transmitting the measured data of the patient via the mobile part to the care device when the patient is removed from the care device.

9. A process according to claim 8, wherein the care device comprises a patient bed and said step of arranging the first receiving means in the vicinity of the patient includes positioning the first receiving means at a location near the bed.

10. A process according to claim 8, wherein the care device comprises means defining a temperature-controlled zone in the region of the bed and a control device for generating a temperature-controlled zone in the environment of a patient and further comprising receiving measured data of the patient from one or both of the removable mobile part and the first receiving means at the control device.

11. A process in accordance with claim 10, further comprising providing a switchover means for changing over from receiving measured data of the patient from the removable mobile part and the first receiving means at the control device.

12. A process in accordance with claim 11, further comprising providing a charging cradle for charging said mobile part wherein said switchover means is a switching contact at said charging cradle, said switching contact responding when said mobile part is removed from said charging cradle or is returned to said charging cradle.

13. A process in accordance with claim 11, wherein said means defining a temperature-controlled zone includes a hood in the region of the bed and said switchover means is a switch responding to an opening or closing of the hood.

14. A care device comprising:
a patient primary care location;
a first receiver arranged adjacent to the patient primary care location;
a sensor module to be placed directly on a patient, said sensor module including at least one sensor for picking up patient data, a power supply unit and a transmitter with a low power for establishing a primary wireless link with the first receiver;
a mobile part having a wireless communication transmitter for establishing a secondary wireless link with the first receiver and a second receiver for establishing an alternative primary wireless link with said sensor module, whereby the patient can move to a location away from said patient primary care location and said mobile part can be moved to near the patient to relay patient data from said sensor module to the first receiver.

15. A care device according to claim 14, further comprising:
a control device for generating a temperature-controlled zone in the region of the patient primary care location, said first receiver for passing on measured data received from said transmitter of said sensor module and/or from said mobile part to said control device.

16. A care device according to claim 14, further comprising: a switchover device changing over between said primary wireless link and said alternative primary wireless link.

17. A care device according to claim 16, further comprising a charging cradle for charging said mobile part wherein said switchover device is a switching contact at said charging cradle, said switching contact responding when said mobile part is removed from said charging cradle or is returned to said charging cradle.

18. A care device in accordance with claim 16, wherein said switchover device is a switch responding to one or more of:
a change in state of medical treatment equipment associated with the care device;
a sensor sensing the presence of the patient at the patient primary care location;
a push button actuated by a user.

19. A care device in accordance with claim 15, wherein the patient primary care location comprises a patient bed with said first receiver at a location near the bed wherein the patient bed is in said temperature-controlled zone in the region of the bed.

20. A care device according to claim 16, further comprising:
a bed and a hood at said patient primary care location, with said first receiver at a location near the bed;
a control device for generating a temperature-controlled zone in the region of said hood, said first receiver for passing on measured data received from said transmitter of said sensor module and/or from said mobile part to said control device, said switchover means including a switch responding to an opening or closing of said hood.

* * * * *